United States Patent [19]

Van Daele

[11] 4,246,429

[45] Jan. 20, 1981

[54] NOVEL α-AMINO-PHENYLACETIC ACID DERIVATIVES

[75] Inventor: Georges Van Daele, Turnhout, Belgium

[73] Assignee: Janssen Pharmaceutica, N.V., Beerse, Belgium

[21] Appl. No.: 28,416

[22] Filed: Apr. 9, 1979

Related U.S. Application Data

[63] Continuation-in-part of Ser. No. 918,530, Jun. 23, 1978, abandoned.

[51] Int. Cl.³ ............... C07C 101/447; C07C 101/453; C07C 101/72; A01N 37/44
[52] U.S. Cl. ............................ 562/456; 260/465 D; 564/74; 564/164; 260/507 R; 564/272; 564/273; 564/274; 560/21; 560/43; 560/44; 562/435; 562/452; 562/457; 562/455; 71/111; 71/112; 71/115; 71/107; 71/67; 71/103; 71/105; 260/501.16; 260/429.7; 260/429.9; 260/438.1; 260/439 R

[58] Field of Search .................. 71/111, 115, 114; 562/456, 457, 435, 452, 455; 260/465 D; 560/43, 21, 44

[56] References Cited

U.S. PATENT DOCUMENTS

| 3,306,909 | 2/1967 | Uloth | 260/326.47 |
| 3,520,922 | 7/1970 | Wagner | 562/452 |
| 3,763,216 | 10/1973 | Bertrand | 562/435 |
| 3,976,468 | 8/1976 | Fischer | 71/111 |
| 4,102,671 | 7/1978 | Haddock | 71/111 |

FOREIGN PATENT DOCUMENTS 53-15325  2/1978  Japan .

OTHER PUBLICATIONS

Takahashi, Chim. Abst., vol. 76, p. 102, #69037d, (1972).

Primary Examiner—James H. Reamer
Attorney, Agent, or Firm—Geoffrey G. Dellenbaugh

[57] ABSTRACT

Novel α-amino-phenylacetic acid derivatives, said phenyl having at least one substituent other than hydrogen, are useful as herbicidal, algicidal and plant growth regulatng agents.

7 Claims, No Drawings

NOVEL α-AMINO-PHENYLACETIC ACID DERIVATIVES

CROSS-REFERENCE TO RELATED APPLICATIONS

This application is a continuation-in-part of our co-pending application Ser. No. 918,530, filed June 23, 1978, now abandoned.

BACKGROUND OF THE INVENTION

In C.A., 76, 69037 d (1972), in U.S. Pat. No. 3,520,922 and in Jap. Pat. No. 7002 199-R there are described a number of α-amino-phenylacetic acid derivatives, wherein said phenyl is unsubstituted, said compounds having herbicidal and fungicidal activities. The compounds of this invention differ therefrom essentially by the presence of at least one substituent on the phenylmoiety. As a result of the presence of said substituent, the compounds of the present invention show, quite unexpectedly, far better herbicidal, algicidal and growth regulating properties than the prior art compounds.

In Japanese Kokai 15325/78 there are described a member of compounds which display antiphlogistic activities and which have a similar structure as the compounds of the present invention.

DESCRIPTION OF THE PREFERRED EMBODIMENTS

This invention relates to novel α-amino-phenylacetic acids and derivatives thereof which may be represented by the formula

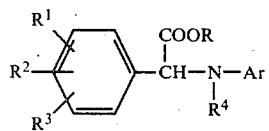

(I)

and the phytopharmaceutically acceptable salts and stereochemically isomeric forms thereof, wherein:
R is selected from the group consisting of hydrogen, $(C_1-C_{20})$-alkyl, $(C_3-C_{20})$-alkenyl, $(C_3-C_{20})$ alkynyl, (lower alkyloxy)-lower alkyl, hydroxy-(lower alkyl), hydroxy-(lower alkyloxy)-lower alkyl, (lower alkyloxy)-carbonyl-lower alkyl, (lower alkyl)-carbonyloxy-(lower alkyl), (mono-, di-, trihalo)-lower alkyl, cycloalkyl, cycloalkyl-(lower alkyl), aryl, aryl-(lower alkyl), aryl-(lower alkenyl), aryl-(lower alkynyl), aryloxy-(lower alkyl), (lower alkyl)-carbonyl-(lower alkyl), aryloxy-carbonyl-(lower alkyl), arylcarbonyl-(lower alkyl), amino-(lower alkyl), mono- and di-(lower alkyl)-amino-(lower alkyl) and $(C_3-C_{20})$-(lower alkenyl)-carbonyloxy;
Ar is selected from the group consisting of aryl, naphthalenyl and substituted naphthalenyl, said substituted naphthalenyl having from 1 to 3 substituents each independently selected from the group consisting of halo, lower alkyl and lower alkyloxy;
$R^1$ is selected from the group consisting of halo, lower alkyl, lower alkyloxy, and trifluoromethyl;
$R^2$ and $R^3$ are each independently selected from the group consisting of hydrogen, halo, lower alkyl, lower alkyloxy, nitro, cyano and amino; and
$R^4$ is a member selected from the group consisting of hydrogen, lower alkyl, aryllower alkyl, lower alkylcarbonyl, halolower alkylcarbonyl, and arylcarbonyl; wherein said aryl as used in the foregoing definitions is selected from the group consisting of phenyl and substituted phenyl, said substituted phenyl having from 1 to 3 substituents each independently selected from the group consisting of halo, lower alkyl, lower alkyloxy, trifluoromethyl, carboxy, carboxy-(lower alkyl), amino, mono- and di(lower alkyl)amino, amino-carbonyl, cyano, nitro, (lower alkyloxy)-carbonyl, (lower alkyloxy)-carbonyl-(lower alkyl), (lower alkyl)-carbonyl and sulfo.

Preferred compounds within the scope of the above defined invention are those wherein R and Ar are as previously defined, $R^1$ is selected from the group consisting of 2-halo, 2-alkyloxy and 2-alkyl, $R^2$ and $R^3$ are each independently selected from the group consisting of hydrogen, halo, lower alkyl, lower alkyloxy and amino, and $R^4$ is hydrogen.

Particularly preferred compounds of formula (I) are those wherein R and Ar are as previously defined, $R^1$ is selected from the group consisting of 2-halo and 2-lower alkyloxy, $R^2$ is 6-halo, $R^3$ is selected from the group consisting of hydrogen, halo, lower alkyl, lower alkyloxy and amino and $R^4$ is hydrogen.

Even more preferred compounds are those wherein R and Ar are as previously defined, $R^1$ is selected from the group consisting of 2-halo and 2-lower alkyloxy, $R^2$ is 6-halo, $R^3$ is 3-halo and $R^4$ is hydrogen.

The most preferred compounds within the above defined invention are those wherein R is hydrogen, Ar is as previously defined, $R^1$ is 2-chloro, $R^2$ is 6-chloro, $R^3$ is 3-chloro and $R^4$ is hydrogen.

As used in the foregoing definitions, the term "halo" is generic to fluoro, chloro, bromo and iodo; "lower alkyl" is meant to include straight and branched hydrocarbon radicals having from 1 to 6 carbon atoms such as, for example, methyl, 1-methylethyl, butyl, hexyl and the like; "lower alkenyl" and "lower alkynyl" are meant to include straight and branched alkenyl, respectively alkynyl, radicals having from 3 to 6 carbon atoms, wherein the unsaturation is preferably located at the β-position, but can also be located at the γ, σ or ε-positions, such as, for example, 2-propenyl, 2-butenyl, 3-methyl-2-butenyl and the like and respectively 2-propynyl, 2-butynyl, 3-methyl-2-butynyl and the like; and the term "cycloalkyl" designates cyclopropyl, cyclobutyl, cyclopentyl and cyclohexyl.

The compounds of formula (I), wherein $R^4$ is hydrogen, said compounds being represented by the formula (I-a), may generally be prepared by hydrolyzing or alcoholyzing an α-aminonitrile of formula (II).

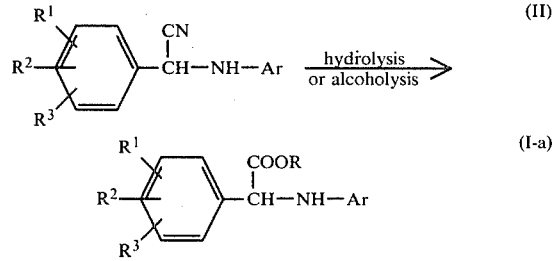

The hydrolysis of the nitrile (II) to the corresponding compound of formula (I-a) wherein R is hydrogen, said compounds being represented by the formula (I-a-1), may be carried out following standard hydrolyzing procedures as generally known in the art, e.g., by stirring and heating the nitrile (II) in a suitable aqueous acidic or alkaline medium. In general, yields can be improved by carrying out the hydrolysis in two steps, more particularly by first hydrolyzing the nitrile to the corresponding amide stage, isolating the latter and subsequently further hydrolyzing said amide (III) to obtain the desired carboxylic acid. The nitrile-to-amide step is preferably carried out in a concentrated aqueous strong acid, e.g., concentrated aqueous sulfuric acid, and the amide-to-acid hydrolysis step is preferably carried out in relatively diluted alkaline medium, e.g., aqueous ethanolic alkali, or said step may also be carried out in acidic medium, e.g., in a solution of hydrochloric acid in glacial acetic acid.

In case the yields in the above procedure are not satisfactorily high said yields can be improved by converting the nitrile (II) into a carbothioamide (IV) by the reaction of the nitrile (II) with gaseous hydrogen sulfide in a suitable solvent, e.g., pyridine and the like, in the presence of an appropriate base, e.g., N,N-diethylethanamine, and at reduced temperature, and converting the thus obtained carbothioamide (IV) into the corresponding carboxylic acid (I-a-1) by an oxidation-reaction with hydrogen peroxide in a suitable reaction-inert solvent such as an alkanol, e.g., methanol and the like, in the presence of an appropriate alkali metal or earth alkaline metal hydroxide, e.g., sodium hydroxide and the like.

The alcoholysis of the nitrile (II), yielding a compound of formula (I-a) wherein R is as previously defined but other than hydrogen, said R being represented by Ra and said compounds by the formula (I-a-2), may be carried out following art-known alcoholyzing-procedures, e.g., by reacting the nitrile (II) with an appropriate alcohol of formula (V), in the presence of an anhydrous strong acid such as, for example, gaseous hydrochloric acid and the like, if desired, in the presence of a suitable reaction-inert solvent such as, for example, a cyclic ether, e.g., tetrahydrofuran and the like.

The compounds of formula (I-a-2) may also be derived from a compound of formula (I-a-1) by reacting the latter with an appropriate alcohol of formula (V) following art-known esterifying procedures. Said esterification reaction may alternatively be prepared by reacting a compound of formula (I-a-1) with a reactive ester of formula (VI) wherein W has the meaning of a reactive ester residue such as, for example, halo, preferably chloro, bromo or iodo, most preferably iodo, or a sulfonyloxy group such as, for example, methylsulfonyloxy, 4-methylphenylsulfonyloxy and the like. Said esterification-reaction is conveniently carried out in the presence of a suitable reaction-inert solvent such as, for example, dimethylformamide, dimethylsulfoxide, hexamethylphosphoric triamide and the like, preferably in the presence of an appropriate strong base such as, for example, an alkali metal or an earth alkaline metal hydride, e.g., sodium hydride and the like. When W is other than iodo it may be advantageous to add an alkali metal or an earth alkaline metal iodide, e.g., sodium iodide and the like.

On the other hand, the compounds of formula (I-a-1) may be derived from a compound of formula (I-a-2) by hydrolyzing the latter in aqueous acidic or alkaline medium, following art-known hydrolysis-procedures. Most preferably, said hydrolysis-reaction is carried out in alkaline medium such as, for example, an aqueous sodium hydroxide solution, if desired, in a water miscible reaction-inert solvent, e.g., a lower alkanol and the like.

The foregoing reactions are schematically illustrated as follows:

The compounds of formula (I) wherein $R^4$ is as previously defined but other than hydrogen, said $R^4$ being represented by $R^4_a$ and said compounds by the formula (I-b), may be derived from a compound of formula (I-a) by reacting the latter with a reagent of formula (VII), wherein W is as previously defined.

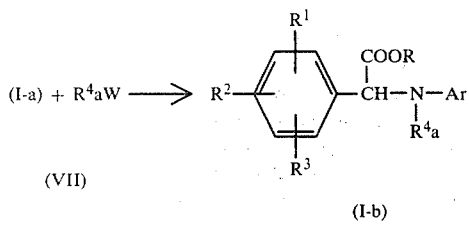

Said reaction may be carried out following standard N-alkylating respectively N-acylating, procedures such as, for example, by stirring and heating the reactants together in the presence of a suitable reaction-inert solvent, e.g., an aliphatic or an aromatic hydrocarbon such as benzene, hexane and the like; an amide, e.g., dimethylformamide, dimethylacetamide and the like.

Obviously, the compounds of formula (I-b), wherein R is hydrogen and $R^4a$ is lower alkyl or aryllower alkyl, may be derived from a corresponding compound of formula (I-b), wherein R is other than hydrogen, following art-known hydrolyzing procedures.

The intermediates of formula (IV), (V), (VI) and (VII) are generally known and they may all be prepared following art-known procedures as described in the literature for the preparation of such known or similar compounds.

The intermediates of formula (II) may generally be prepared by reacting an appropriately substituted benzaldehyde of formula (VIII) with an appropriate amine of formula (IX) in the presence of an appropriate cyanide such as, for example, an alkali metal- or earth alkaline metal cyanide, e.g., sodium or potassium cyanide.

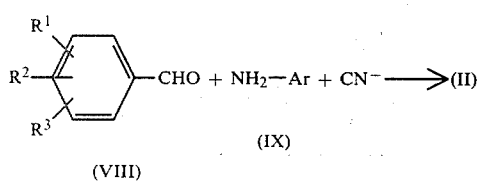

Said reaction is conveniently carried out by stirring and, if desired, heating the reactants together in the presence of a suitable relatively polar reaction-inert solvent such as, for example, glacial acetic acid, water and the like, or a mixture of two or more relatively polar solvents.

When the amine (IX) is a weakly basic amine, it is advantageous to carry out the reaction in the presence of an anhydrous zinc halide, e.g., zinc chloride, in a relatively polar anhydrous solvent, e.g., glacial acetic acid.

The intermediates of formula (II) may alternatively be prepared by the reduction of an appropriate α-iminonitrile (X). The latter may be prepared following art-known procedures as described in the literature for the preparation of such known or similar compounds, e.g., by reacting an appropriate N-arylbenzamide (XI) with an halogenating agent and subsequently converting the thus obtained imidoyl halide (XII) into an α-iminonitrile (X).

The foregoing reactions are illustrated as follows:

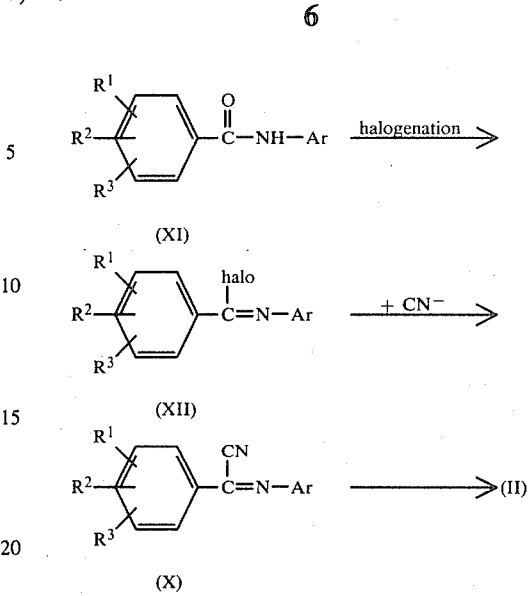

The above halogenation step may be carried out by the reaction of (XI) with an appropriate halogenating agent such as, for example, by stirring and heating the amide (XI) with phosphorpentachloride while the formed phosphoryl chloride is removed by destillation.

The substitution of halo by cyano may be carried out in a two phase-solvent system in the presence of a phase-transfer catalyst as described in Synthesis 1978, 894.

The reduction reaction may conveniently be carried out with an appropriate complex metal hydride, e.g., sodium borohydride, lithium borohydride, lithium aluminium hydride and the like in the presence of a suitable solvent. Such a reaction-procedure is described in Chemistry and Industry, 1975, 569.

It is obvious from formula (I) that the compounds of this invention have at least one asymmetric carbon atom within their structure, more particularly the carbon atom in the α-position relative to the carboxyl-function, and consequently they may exist under at least two different enantiomeric forms. Pure enantiomeric forms of the compounds (I) may be obtained by the application of art-known procedures such as, for example, separation of their diastereomeric salts with optically active acids or bases or of diastereomeric esters of the carboxylic acids (I-a) with optically active alcohols. Isomers of compounds of formula (I) are naturally intended to be embraced within the scope of this invention.

Due to the presence of a weakly basic amine group within their structure the compounds of formula (I) are able to form addition salts with relatively strong acids such as, for example, an inorganic acid, e.g., hydrochloric, hydrobromic, hydroiodic, sulfuric, nitric, chloric, thiocyanic, phosphoric and the like acids; and organic acids such as, for example, sulfonic acids, e.g., methanesulfonic, ethanesulfonic, 4-methylbenzenesulfonic and naphthalenesulfonic acid.

The compounds of formula (I) wherein R represents hydrogen may also form salts with appropriate bases. For example, they may form addition salts with suitable basic amines such as, for example, alkylamines, e.g., mono-, di- and tri-ethylamine, mono- and di-(1-methylethyl)amine; mono-, di- and tri-ethanolamine; pyridine and methylpyridine; aniline and naphthalenamine; and the like. They may also form metal salts such as for example, lithium, sodium, potassium, calcium, magnesium, manganese, iron, copper, zinc, tin and the like salts. The phytopharmaceutically acceptable salts of compounds of formula (I) are naturally intended to fall within the scope of the present invention.

The compounds of formula (I) and the phytopharmaceutically acceptable salts thereof are potent herbicides, algicides and plant-growth regulators. They show particularly good herbicidal activity against a wide variety of weeds such as, for example, Polygonacease, e.g., *Polygonum persicaria;* Plantaginaceae, e.g., *Plantago major* and *P. lanceolata;* Rubiacea, e.g., *Galium aparine;* Caryophyllaceae, e.g. *Stellaria media;* Hyperiacea, e.g., *Hypericum perforatum;* Compositae, e.g., Galiusoga sp., *Achillea millefolium* and *Matricaria inodera;* Graminea, e.g., *Echinocloa crusgalli* and *Agrostis tenuis;* Chenopodiaceae, e.g., *Chenopodium album;* Labiatae, e.g., Lamium sp.; Cruciferae, e.g., *Capsella bursa-pastoris;* and Solanaceae, e.g., *Solanum nigrum.*

The subject compounds may be used as pre-emergence and as post-emergence herbicides. Preferably they are used in a pre-emergence application. They may also be used as growth regulators, e.g., to reduce the longitudinal growth of cereals in order to make them more resistant to lodging.

The useful herbicidal and plant-growth-regulating activities of the compounds of the present invention are clearly demonstrated in the following experiment wherein their activity against a number of cultivated plants was investigated. It is noted that the species used in the experiment are only selected as representatives of their respective plant families to which also belong an important number of major weeds.

Pre-emergence herbicidal test

Seeds of different plant species are sown in plastic pots ($13 \times 13 \times 13$ cm$^3$) filled with sandy soil. Immediately thereafter the pots are watered with an aqueous solution comprising the test solution at a concentration equivalent with an overal dose of 4 kg/ha. The pots are kept in the greenhouse and possible herbicidal or growth regulating activity of the test compounds is evaluated 4 weeks after sowing using the following score system.

| Score | % growth reduction as compared with untreated controls |
|---|---|
| 1 | 0 |
| 2 | 2.5 |
| 3 | 5 |
| 4 | 10 |
| 5 | 15 |
| 6 | 25 |
| 7 | 35 |
| 8 | 67.5 |
| 9 | 100 |

The results obtained with a number of the subject compounds on certain plant species are taken up in the following table. It is evident that the compounds listed therein are not given for the purpose of limiting the invention thereto but only to exemplify the useful herbicidal and growth regulating properties of the compounds within the scope of formula (I).

TABLE I

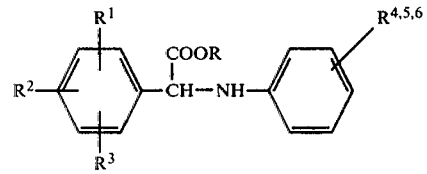

| $R^1$, $R^2$, $R^3$ | $R^{4,5,6}$ | R | | Oats | Italian Ryegrass | Lucern | rape | andive | tomato | beet |
|---|---|---|---|---|---|---|---|---|---|---|
| 2-Cl | 2,4-Cl$_2$ | H | | 1 | 1 | 1 | 7 | 1 | 1 | 1 |
| 2-Cl | 2,4,5-Cl$_3$ | H | | 1 | 1 | 9 | 1 | 1 | 1 | 1 |
| 2-Cl | 2-CH$_3$, 5-Cl | H | | 1 | 1 | 1 | 1 | 7 | 1 | 1 |
| 2-Cl | 2-Cl, 4-CH$_3$ | H | | 1 | 1 | 1 | 1 | 7 | 1 | 1 |
| 3-Cl | 2,5-Cl$_2$ | H | | 1 | 1 | 7 | 1 | 1 | 1 | 1 |
| 2,3,6,-Cl$_3$ | 2-CH$_3$ | H | | 6 | 1 | 9 | 9 | 9 | 9 | 9 |
| 2,6-Cl$_2$ | 2-Cl | H | | 1 | 1 | 8 | 1 | 1 | 7 | 8 |
| 2,6-Cl$_2$ | 3-Cl | H | | 1 | 1 | 9 | 1 | 1 | 7 | 8 |
| 2,6-Cl$_2$ | 4-Cl | H | | 1 | 1 | 1 | 1 | 1 | 7 | 7 |
| 2,6-Cl$_2$ | 2,5-Cl$_2$ | H | | 1 | 1 | 7 | 7 | 8 | 7 | 8 |
| 2,6-Cl$_2$ | 3,4-Cl$_2$ | H | | 1 | 1 | 9 | 1 | 1 | 8 | 8 |
| 2,6-Cl$_2$ | 3,5-Cl$_2$ | H | | 1 | 1 | 9 | 1 | 7 | 7 | 8 |
| 2,6-Cl$_2$ | 2,4,5-Cl$_3$ | H | | 1 | 1 | 8 | 1 | 1 | 7 | 7 |
| 2,6-Cl$_2$ | 4-Br | H | | 1 | 1 | 8 | 6 | 7 | 7 | 8 |
| 2,6-Cl$_2$ | 4-I | H | | 1 | 1 | 9 | 6 | 1 | 7 | 5 |
| 2,6-Cl$_2$ | 2-CH$_3$ | H | | 1 | 1 | 8 | 6 | 6 | 7 | 7 |
| 2,6-Cl$_2$ | 2,5-(CH$_3$)$_2$ | H | | 4 | 4 | 9 | 6 | 8 | 8 | 6 |
| 2,6-Cl$_2$ | 3,4-(CH$_3$)$_2$ | H | | 1 | 1 | 8 | 1 | 1 | 6 | 5 |
| 2,6-Cl$_2$ | 2,4-(CH$_3$)$_2$ | H | | 1 | 1 | 8 | 6 | 7 | 8 | 7 |
| 2,6-Cl$_2$ | 2-CH$_3$, 4-Cl | H | | 1 | 1 | 8 | 9 | 8 | 8 | 7 |
| 2,6-Cl$_2$ | 3-CH$_3$, 4-Cl | H | | 1 | 1 | 8 | 8 | 7 | 7 | 7 |
| 2,6-Cl$_2$ | 2-Cl, 4-CH$_3$ | H | | 1 | 3 | 8 | 1 | 8 | 7 | 6 |
| 2,6-Cl$_2$ | 3-Cl, 4-CH$_3$ | H | | 1 | 1 | 8 | 4 | 7 | 7 | 7 |
| 2,6-Cl$_2$ | 2-Cl, 5-CF$_3$ | H | | 1 | 1 | 8 | 9 | 9 | 8 | 7 |
| 2,6-Cl$_2$ | 3-CH(CH$_3$)—COOH | H | | 1 | 1 | 7 | 6 | 7 | 7 | 3 |
| 2,6-Cl$_2$ | 2-Cl, 3-CH(CH$_3$)—COOH | H | | 1 | 1 | 9 | 9 | 1 | 8 | 7 |
| 2,6-Cl$_2$ | 3,4-(CH=CH—CH=CH) | H | + isomer | 1 | 1 | 9 | 7 | 8 | 7 | 6 |
| 2,6-Cl$_2$ | 3,4-(CH=CH—CH=CH) | H | − isomer | 1 | 1 | 7 | 7 | 8 | 7 | 9 |
| 4-Br | 2-COOH | H | | 1 | 1 | 1 | 8 | 1 | 1 | 1 |
| 2,6-Cl$_2$ | 3-Cl | CH$_3$ | | 1 | 1 | 7 | 1 | 1 | 8 | 5 |

TABLE I-continued $$R^2 \underset{R^3}{\overset{R^1}{\underset{}{\bigcirc}}} - \underset{\underset{CH-NH}{|}}{\overset{COOR}{|}} - \bigcirc - R^{4,5,6}$$

| $R^1$, $R^2$, $R^3$ | $R^{4,5,6}$ | R | Plant species/score | | | | | | |
|---|---|---|---|---|---|---|---|---|---|
| | | | Oats | Italian Ryegrass | Lucern | rape | andive | tomato | beet |
| 2,6-Cl$_2$ | 3-Cl | C$_4$H$_9$ | 1 | 1 | 1 | 6 | 1 | 1 | 8 |
| 2,6-Cl$_2$ | 3-Cl | C$_6$H$_{13}$ | 1 | 1 | 9 | 1 | 7 | 1 | 1 |
| 2,6-Cl$_2$ | 3-Cl | C$_{10}$H$_{21}$ | 1 | 1 | 1 | 1 | 7 | 1 | 1 |
| 2,3,6-Cl$_3$ | 2-CH$_3$ | Na | 6-7 | 1 | 9 | 9 | 9 | 9 | 9 |
| 2,3,6-Cl$_3$ | 2,5-(CH$_3$)$_2$ | H | 3 | 6 | 9 | 7-9 | 8-9 | 9 | 7-8 |
| 2,3,6-Cl$_3$ | 3-CF$_3$ | H | 3 | 7 | 9 | 9 | 9 | 8-9 | 8 |
| 2,3,6-Cl$_3$ | 4-Br | H | 3 | 7-8 | 9 | 8-9 | 9 | 8-9 | 8-9 |
| 2,3,6-Cl$_3$ | H | H | — | 8 | 9 | 9 | 9 | 9 | 9 |
| 2,3,6-Cl$_3$ | 2-CH$_3$ | C$_9$H$_{19}$ | 1 | 1 | 5 | 9 | 4 | 9 | 8-9 |
| 2,3,6-Cl$_3$ | 4-Br | C$_2$H$_5$ | 1 | 1 | 7-8 | 6 | 5 | 6 | 6 |
| 2,3,6-Cl$_3$ | 2-CH$_3$ | CH$_3$ | 1 | 1 | 8-9 | 7 | 3 | 8-9 | 7-8 |

In view of the aforementioned herbicidal, growth regulating and algicidal activities, this invention provides valuable compositions comprising compounds of formula (I) and salts thereof as the active ingredient in a solvent or a solid, semi-solid or liquid diluent or carrier. In addition it provides an effective method of combatting weeds and algae or regulating the growth of plants by use of an effective herbicidal, algicidal or growth regulating amount of a compound of formula (I) or salt thereof.

The subject compounds can be used in suitable solvents or diluents, in the form of emulsions, suspensions or dispersions. They may also be used in powder form in which case there may be used suitable solid carrier substances, including various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr, clay and boric acid; powdered cork, sawdust, and other fine pulverous materials of vegetable origin are also suitable carrier substances. By adding wetting and/or dispersing agents, pulverous preparations can also be made readily wettable with water, so that suspensions are obtained.

Inert solvents used for the production of liquid preparations should preferably not be readily inflammable and as far as possible non-toxic to warm-blooded animals. Solvents suitable for this purpose include high-boiling oils, for example, oils of vegetable origin, and lower-boiling solvents, such as, for example, isopropanol, dimethylsulfoxide, hydrogenated naphthalenes, alkylated naphthalenes, alkoxyalkanols, etc . . . It is of course, also possible to use mixtures of solvents. Solutions can be prepared in the usual way, if necessary, with assistance of solution promoters. Other liquid forms which can be used consist of emulsions or suspensions of the active compound in water or suitable inert solvents, or also concentrates for preparing such emulsions, which can be directly adjusted to the required concentration. For this purpose, the compound of formula (I) or salt thereof is, for example, mixed with a dispersing or emulsifying agent. The active component can also be dissolved or dispersed in a suitable inert solvent and mixed simultaneously or subsequently with a dispersing or emulsifying agent. The compounds of the present invention may also be used in the form of granulates or microgranulates.

When the compounds are employed in combination with suitable carriers, e.g., in solution, emulsion, suspension, dust, granulate and the like forms, a high activity over a very broad range of dilution is observed. Effective compositions according to the present invention may contain from about 0.001 to about 15% and preferably from about 0.01 to about 10% of the active ingredient. Of course, higher concentrations may be employed as warranted by the particular situation. Commercial preparations can contain from about 0.1 to about 95% and preferably from about 1 to about 80% of the active ingredient. Preferred commercial preparations are concentrated forms, containing from about 5 to about 90% and peferably from about 10 to about 70% of the active ingredient.

The following examples are intended to illustrate and not to limit the scope of the present invention. Unless otherwise indicated all parts therein are by weight.

EXAMPLE I

To a stirred mixture of 17.4 parts of methyl 2-aminobenzoate 18.5 parts of 4-bromobenzaldehyde in 200 parts of glacial acetic acid is added dropwise a solution of 8.15 parts of potassium cyanide in 15 parts of water, while keeping the temperature below 16° C. Upon completion, stirring is continued for 19 hours at room temperature. The precipitated product is filtered off, washed with 2,2'-oxybispropane and dried in vacuo, yielding 25 parts of methyl 2-{[(4-bromophenyl)-cyanomethyl]amino}benzoate; mp. 111.5° C.

EXAMPLE II

Following the procedure of Example I and using equivalent amounts of the appropriate starting materials, the following compounds are prepared:

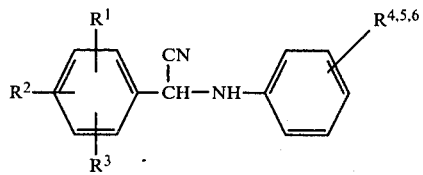

| R¹, R², R³ | R⁴,⁵,⁶ | melting point in °C. |
| --- | --- | --- |
| 4-Cl | 2-COOCH₃ | 92.5 |
| 2,4-Cl₂ | 2-COOCH₃ | 110.5 |
| 3,4-Cl₂ | 2-COOCH₃ | 103 |
| 2,6-Cl₂ | 2-Cl,5-CH(CH₃)—C(O)—OC₂H₅ | — |
| 2-Cl | 2-F,5-CH(CH₃)—COOC₂H₅ | — |
| 2,6-Cl₂ | — | 114 |
| 2,6-Cl₂ | 2,4-(CH₃)₂ | 94 |
| 2,6-Cl₂ | 3,4-(CH₃)₂ | 82.5 |
| 2,6-Cl₂ | 3-CF₃ | 100.5 |
| 2,6-Cl₂ | 3-CH₃,4-Cl | 123 |
| 2,6-Cl₂ | 2,5-(CH₃)₂ | 121.5 |
| 2,6-Cl₂ | 3-Cl, 4-CH₃ | 134 |
| 2,6-Cl₂ | 2-CH₃, 3-Cl | 125 |
| 2,6-Cl₂ | 4-Cl | 101.5 |
| 2,6-Cl₂ | 3-Cl | 128 |
| 2,6-Cl₂ | 2-CH₃, 4-Cl | 103 |
| 2,6-Cl₂ | 2-CH₃ | 107.5 |
| 2,6-Cl₂ | 2-OCH₃ | 117.5 |
| 2,6-Cl₂ | 2,3-(CH₃)₂ | 101 |
| 2,6-Cl₂ | 3-CH₃ | 85.5 |
| 2,4-Cl₂ | 2-CH₃ | 124.3 |
| 2,4-Cl₂ | — | 116.6 |
| 2,4-Cl₂ | 4-Cl | 80 |
| 2,4-Cl₂ | 3-Cl | 94.8 |
| 2,4-Cl₂ | 3-CH₃ | 95 |
| 2,4-Cl₂ | 2-Cl | 102.6 |
| 2,4-Cl₂ | 2,5-(CH₃)₂ | — |
| 2,6-Cl₂ | 4-Br | 105.5 |
| 2-Cl | 4-SO₃K | —acetate |
| 2,6-Cl₂, 3-NO₂ | 4-Cl | 127.9 |
| 2,6-Cl₂ | 4-CH₃ | 109 |
| 2,3,6-Cl₃ | 2-CH₃ | 125 |
| 2-Cl | 2-Cl, 4-CH₃ | 105.9 |
| 2-Cl | 3-CH₃ | 96.9 |
| 2-Cl | 3,4-(CH₃)₂ | 126.4–128.4 |
| 2-Cl | 3-Cl | 93.9 |
| 2-Cl | 2,5-(CH₃)₂ | 155.2 |
| 2-Cl | 2-Cl | 83.1–87.2 |
| 2-Cl | 2-CH₃ | 128.3 |
| 2-Cl | 2-CH₃, 4-Cl | 141 |
| 2-Cl | 3-Cl, 4-CH₃ | 126.5 |
| 2-Cl | 3,4-Cl₂ | 125.2 |
| 2-Cl | 2,3-(CH₃)₂ | 129.4–134.7 |
| 2-Cl | 4-CH₃ | 88.4–90.2 |
| 2-Cl | 4-Cl | 179.4 |
| 2,6-Cl₂ | 2-Cl | 87.5 |
| 2,6-Cl₂ | 2-OCH₃, 5-CH₃ | 119.5 |
| 2-Cl | 2,3-Cl₂, 5-COOCH₃ | 170 |
| 2-Cl | 2,4-Cl₂, 5-COOCH₃ | — |
| 2,3,4-Cl₃ | 2-CH₃ | 160 |
| 2,6-Cl₂ | 2,6-(CH₃)₂ | 118.5° |
| 4-(t. butyl) | 4-[CH(CH₃)COOC₂H₅] | 120 |
| 2,3,6-Cl₃ | 2,5-(CH₃)₂ | — |
| 2,3,6-Cl₃ | 4-Cl-3-(CH₃) | 103 |
| 2,3,6-Cl₃ | 3-CF₃ | 118 |
| 2,3,6-Cl₃ | H | — |
| 2,3,6-Cl₃ | 4-Br | 164 |

EXAMPLE III

To a stirred mixture of 43.8 parts of 2,6-dichlorobenzaldehyde, 41 parts of 2-naphthalenamine and 500 parts of glacial acetic acid is added dropwise a solution of 20.3 parts of potassium cyanide in 35 parts of water. The whole is stirred for 40 hours at room temperature. The precipitated product is filtered off, washed on the filter with glacial acetic acid, with 2-propanol and petrleum ether, and dried, yielding 60 parts of 2,6-dichloro-α-[(2-naphthalenyl)amino]benzeneacetonitrile; mp. 94.8° C.

EXAMPLE IV

To a stirred mixture of 53 parts of benzaldehyde in 820 parts of water are added successively 78.6 parts of 2,4,5-trichlorobenzenamine, 81.8 parts of zinc chloride and 32.6 parts of potassium cyanide and the whole is stirred for 18 hours at 50° C. The reaction mixture is cooled to room temperature. The precipitated product is filtered off, triturated in 1000 parts of water, filtered off again and dissolved in 750 parts of trichloromethane. The solution is washed twice with water, dried, filtered and evaporated. The solid residue is triturated in petroleum ether, filtered off again and dried, yielding 83.1 parts of α-[(2,4,5-trichlorophenyl)amino]benzeneacetonitrile; mp. 123.7° C.

EXAMPLE V

Following the procedure of Example IV and using equivalent amounts of the appropriate starting materials, the following compounds are prepared.

| R¹, R², R³ | R⁴,⁵,⁶ | melting point in °C. |
| --- | --- | --- |
| 2,4-Cl₂ | 2,6-Cl₂ | 131 |
| 2-Cl | 2,6-Cl₂ | 70 |
| 4-Cl | 2,4,6-Cl₃ | 129.1 |
| 2,4-Cl₂ | 2,4,5-Cl₃ | 132.7 |
| 2,6-Cl₂ | 3,4-Cl₂ | 135.5 |
| 4-Cl | 2,4,5-Cl₃ | 140.3 |
| 4-CH₃ | 2,4,5-Cl₃ | 104.6 |
| 2,6-Cl₂ | 2,5-Cl₂ | 138 |
| 3-Cl | 2,4,5-Cl₃ | 140.6 |
| 2-Cl | 2-CH₃,3-Cl | 153.7 |
| 3-Cl | 2-CH₃,3-Cl | 122.5 |
| 2-Cl | 2,3-Cl₂ | 132.5 |
| 3-Cl | 2,6-Cl₂ | 79.4 |
| 3,4-Cl₂ | 2-CH₃,3-Cl | 141.3 |
| 2-Cl | 2,5-Cl₂ | 156.5 |
| 3,4-Cl₂ | 2,5-(CH₃)₂ | 143.7 |
| 3,4-Cl₂ | 2,6-Cl₂ | 104.1 |
| 3-Cl | 2,5-Cl₂ | 139.4 |
| 2-Cl | 2,4-Cl₂ | 117 |

| R¹, R², R³ | R⁴,⁵,⁶ | melting point in °C. |
| --- | --- | --- |
| 3-Cl | 4-Cl | 69.3 |
| 3-Cl | 2,5-(CH₃)₂ | 120.1 |
| 2,4-Cl₂ | 2-CH₃,3-Cl | 146.1 |
| 2-CH₃ | 2,4,5-Cl₃ | 129 |
| 2,6-Cl₂ | 2,4,5-Cl₃ | 162.8 |
| 3,4-Cl₂ | 2,3-Cl₂ | 154.8 |
| 2,5-Cl₂ | 2,4,5-Cl₃ | 175.2 |
| 2-Cl | 2-Cl,5-CF₃ | 125 |
| 2-Cl | 2-CH₃,5-Cl | 174.8 |
| 2-Cl | 3,5-Cl₂ | 156 |
| 2,6-Cl₂ | 3,5-Cl₂ | 134.4 |
| 2,6-Cl₂ | 2-CH₃,5-Cl | 116 |
| 2,6-Cl₂ | 2-Cl,5-CF₃ | 130 |
| 2-OCH₃ | 2,4,5-Cl₃ | 135.2 |
| 2-Cl | 2,4,5-Cl₃ | 132.2 |
| 2,6-Cl₂ | 4-I | 118–120 |

-continued

| $R^1$, $R^2$, $R^3$ | $R^{4,5,6}$ | melting point |
|---|---|---|
| 2-F | 2,4,5-Cl$_3$ | 120 |
| 2-OCH$_3$ | 3,4-Cl$_2$ | 135 |
| 2-Cl,4-CH$_3$ | 2,4,5-Cl$_3$ | 110.5 |
| 2-Cl,6-CH$_3$ | 2,4,6-Cl$_3$ | 148 |
| 2,6-Cl$_2$ | 2-Cl,4-CH$_3$ | 60 |
| 2,3,6-Cl$_3$ | 3,5-Cl$_2$ | 134 |
| 2,3,6-Cl$_3$ | 2,5-Cl$_2$ | 149 |

EXAMPLE VI

50 Parts of 2,6-dichloro-α-[(4-chlorophenyl)amino]-benzeneacetonitrile are added portionwise to 270 parts of sulfuric acid/water (10:1 by volume) and the whole is stirred overnight at room temperature. The reaction mixture is poured onto 2000 parts of ice-water. The precipitated product is filtered off, washed on the filter successively with water and 2-propanol and recrystallized from 560 parts of 2-propanol at −20° C., yielding 43.1 parts of 2,6-dichloro-α-[(4-chlorophenyl)amino]-benzeneacetamide; mp. 178° C.

EXAMPLE VII

Following the procedure of Example VI and using equivalent amounts of the appropriate starting materials, the following compounds are prepared:

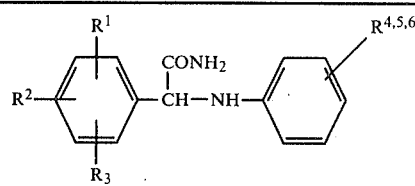

| $R^1$, $R^2$, $R^3$ | $R^{4,5,6}$ | melting point in °C. |
|---|---|---|
| 2,6-Cl$_2$ | 2-Cl,5-CH(CH$_3$)—COOC$_2$H$_5$ | 134.7 |
| 2-Cl | 2-F,5-CH(CH$_3$)—COOC$_2$H$_5$ | 110.5 |
| 2,6-Cl$_2$ | 3-CH(CH$_3$)—COOC$_2$H$_5$ | 109.6 |
| 2-COOCH$_3$ | 2,4-Cl$_2$ | 141.5 |
| 2-COOCH$_3$ | 3,4-Cl$_2$ | 173 |
| 2-COOCH$_3$ | 4-Cl | 198 |
| 2-COOCH$_3$ | 4-Br | 208.5 |
| 2,6-Cl$_2$ | — | 148.5 |
| 2,6-Cl$_2$ | 2,4-(CH$_3$)$_2$ | 170.5 |
| 2,6-Cl$_2$ | 3,4-(CH$_3$)$_2$ | 180 |
| 2,6-Cl$_2$ | 3-CF$_3$ | 142.5 |
| 2,6-Cl$_2$ | 3-CH$_3$, 4-Cl | 160 |
| 2,6-Cl$_2$ | 2,5-(CH$_3$)$_2$ | 187 |
| 2,6-Cl$_2$ | 3-Cl, 4-CH$_3$ | 157.5 |
| 2,6-Cl$_2$ | 2-CH$_3$, 3-Cl | 167.5 |
| 2,6-Cl$_2$ | 3-Cl | 147 |
| 2,6-Cl$_2$ | 2-CH$_3$, 4-Cl | 182 |
| 2,6-Cl$_2$ | 2-CH$_3$ | 170 |
| 2,6-Cl$_2$ | 2-OCH$_3$ | 192 |
| 2,6-Cl$_2$ | 2,3-(CH$_3$)$_2$ | 194 |
| 2,6-Cl$_2$ | 3-CH$_3$ | 163.5 |
| 2,4-Cl$_2$ | 2-CH$_3$ | 173 |
| 2,4-Cl$_2$ | — | 156.1 |
| 2,4-Cl$_2$ | 4-Cl | 144.8 |
| 2,4-Cl$_2$ | 2,6-Cl$_2$ | 158.6 |
| 2-Cl | 2,6-Cl$_2$ | 148.5 |
| 4-Cl | 2,4,6-Cl$_3$ | 149 |
| 2,4-Cl$_2$ | 2,4,5-Cl$_3$ | 192 |
| 2,6-Cl$_2$ | 3,4-Cl$_2$ | 172.4 |
| 4-Cl | 2,4,5-Cl$_3$ | 192.5 |
| 4-CH$_3$ | 2,4,5-Cl$_3$ | 149 |
| 2,6-Cl$_2$ | 2,5-Cl$_2$ | 193.8 |
| 2,4-Cl$_2$ | 3-Cl | 118–7 |
| 2,4-Cl$_2$ | 3-CH$_3$ | 137.3 |
| 2,4-Cl$_2$ | 2-Cl | 150.3 |
| 3-Cl | 2,4,5-Cl$_3$ | 125.9 |
| 2-Cl | 2-CH$_3$, 3-Cl | 180 |
| 3-Cl | 2-CH$_3$, 3-Cl | 122.5 |
| 2-Cl | 2,3-Cl$_2$ | 155.9 |
| 3-Cl | 2,6-Cl$_2$ | 121 |
| 3,4-Cl$_2$ | 2-CH$_3$, 3-Cl | 134.2 |
| 2-Cl | 2,5-Cl$_2$ | 177.1 |
| 3,4-Cl$_2$ | 2,5-(CH$_3$)$_2$ | 153 |
| 2,4-Cl$_2$ | 2,5-(CH$_3$)$_2$ | 147.5 |
| 3,4-Cl$_2$ | 2,6-Cl$_2$ | 109.3 |
| 3-Cl | 2,5-Cl$_2$ | 134.5 |
| 2-Cl | 2,4-Cl$_2$ | 168 |
| 3-Cl | 4-Cl | 131.1 |
| 3-Cl | 2,5-(CH$_3$)$_2$ | 115 |
| 2,4-Cl$_2$ | 2-CH$_3$, 3-Cl | 153.2 |
| 2-CH$_3$ | 2,4,5-Cl$_3$ | 192.3 |
| 2,6-Cl$_2$ | 2,4,5-Cl$_3$ | 225.4 |
| 3,4-Cl$_2$ | 2,3-Cl$_2$ | 147.2 |
| 2,5-Cl$_2$ | 2,4,5-Cl$_3$ | 197.1 |
| 2-Cl | 2-Cl, 5-CF$_3$ | 137.6 |
| 2-Cl | 2-CH$_3$, 5-Cl | 157 |
| 2-Cl | 3,5-Cl$_2$ | 146 |
| 2,6-Cl$_2$ | 3,5-Cl$_2$ | 180.9 |
| 2,6-Cl$_2$ | 2-CH$_3$, 5-Cl | 211.2 |
| 2,6-Cl$_2$ | 2-Cl, 5-CF$_3$ | 173 |
| 2-Cl | 2,4,5-Cl$_3$ | 213.1 |
| 2,6-Cl$_2$ | 4-Br | 167.5 |
| 2,6-Cl$_2$ | 4-I | 150.1 |
| 2-F | 2,4,5-Cl$_3$ | 152.9 |
| 2,6-Cl$_2$, 3-NO$_2$ | 4-Cl | 152.6 |
| 2,4-Cl$_2$ | 4-CH$_3$ | 148 |
| 2-Cl,4-CH$_3$ | 2,4,5-Cl$_3$ | 170 |
| 2-Cl,6-CH$_3$ | 2,4,5-Cl$_3$ | 204.8 |
| 2,3,6-Cl$_3$ | 2-CH$_3$ | 171.9 |
| 2-Cl | 2-Cl, 4-CH$_3$ | 171.1 |
| 2-Cl | 3-CH$_3$ | 132 |
| 2-Cl | 3,4-(CH$_3$)$_2$ | 154 |
| 2-Cl | 3-Cl | 112.1 |
| 2-Cl | 2,5-(CH$_3$)$_2$ | 170.8 |
| 2-Cl | 2-Cl | 149.9 |
| 2-Cl | 2-CH$_3$ | 153.5 |
| 2-Cl | 2-CH$_3$, 4-Cl | 167.7 |
| 2-Cl | 3-Cl, 4-CH$_3$ | 127.8 |
| 2-Cl | 3,4-Cl$_2$ | 134.2 |
| 2-Cl | 2,3-(CH$_3$)$_2$ | 202.7 |
| 2-Cl | 4-CH$_3$ | 154.2 |
| 2-Cl | 4-Cl | 123.5 |
| 2,6-Cl$_2$ | 2-Cl | 166 |
| 2,6-Cl$_2$ | 2-Cl, 4-CH$_3$ | 170 |
| 2,6-Cl$_2$ | 2-OCH$_3$, 5-CH$_3$ | 197 |
| 2-Cl | 2,3-Cl$_2$, 5-COOCH$_3$ | 184.6 |
| 2-Cl | 2,4-Cl$_2$, 5-COOCH$_3$ | — |
| 2,3,4-Cl$_3$ | 2-CH$_3$ | 140 |
| 2,6-Cl$_2$ | 2,6-(CH$_3$)$_2$ | 232 |
| 4-t.butyl | 4-CH(CH$_3$)COOC$_2$H$_5$ | 150 |

EXAMPLE VIII

To 360 parts of concentrated sulfuric acid are added portionwise 30 parts of 2,6-dichloro-α-[(2-naphthalenyl)amino]benzeneacetonitrile and the whole is stirred till all solid enters solution. The reaction solution is allowed to stand overnight at room temperature and then poured onto 1000 parts of crushed ice. The precipitated product is filtered off and extracted with 1500 parts of chloroform. The organic phase is washed with water, dried, filtered and evaporated. The oily residue solidifies on triturating in 2-propanol. The solid product is filtered off and crystallized from 200 parts of 2-propanol at 0° C., yielding 11.3 parts of 2,6-dichloro-α-[(2-naphthalenyl)amino]benzeneacetamide; mp. 157.9° C.

In a similar manner there are also prepared:

2,3,6-trichloro-α-[(2,5-dimethylphenyl)amino]benzeneacetamide; mp. 163.3° C.;
2,3,6-trichloro-α-[(4-chloro-3-methylphenyl)amino]benzeneacetamide; mp. 142° C.;
2,3,6-trichloro-α-{[3-(trifluoromethyl)phenyl]amino}-benzeneacetamide; mp. 99.2° C.;
2,3,6-trichloro-α-[(3,5-dichlorophenyl)amino]benzeneacetamide; mp. 139.4° C.;
2,3,6-trichloro-α-[(2,5-dichlorophenyl)amino]benzeneacetamide; mp. 171.6° C.;
2,3,6-trichloro-α-(phenylamino)benzeneacetamide; mp. 169.4° C.; and
α-[(4-bromophenyl)amino]-2,3,6-trichlorobenzeneacetamide; mp. 171.8° C.

EXAMPLE IX

To a stirred and refluxed mixture of 37.5 parts of 2,6-dichloro-α-[(4-chlorophenyl)amino]-3-nitrobenzeneacetamide, 500 parts of an ammonium chloride solution 1 N and 800 parts of methylbenzene are added 28 parts of iron powder. Upon completion, stirring at reflux is continued for 50 minutes. The reaction mixture is filtered and the crystallized product is filtered off from the filtrate. It is boiled in 1000 parts of methylbenzene: one part dissolves, but crystallized again upon cooling to room temperature. It is filtered off and dried, yielding 7.1 parts of 3-amino-2,6-dichloro-α-[(4-chlorophenyl)amino]benzeneacetamide; mp. 231.8° C.

EXAMPLE X

A mixture of 12.1 parts of 2-methoxy-α-[(2-methylphenyl)amino]-1-naphthaleneacetonitrile, 4.1 parts of N,N-diethylethanamine and 20 parts of dry pyridine is stirred and cooled to 0° C. (cooling in a 2-propanone/-CO$_2$-bath). During 2 hours, gaseous hydrogen sulfide is introduced. The whole is stored overnight at 0° C. The reaction mixture is poured onto 600 parts of water. The precipitated product is filtered off and dissolved in 450 parts of trichloromethane. The solution is washed with 100 parts of water, dried, filtered and evaporated. The residue is crystallized from 120 parts of acetonitrile. The product is filtered off (the filtrate is set aside) and dried, yielding a first fraction of 6.9 parts of 2-methoxy-α-[(2-methylphenyl)amino]-1-naphthalenecarbothioamide.

The filtrate which was set aside (see above) is evaporated. The residue is suspended in 40 parts of 2-propanol. The product is filtered off and dried, yielding a second fraction of 5.4 parts of 2-methoxy-α-[(2-methylphenyl)amino]-1-naphthalenecarbothioamide.

Total yield: 12.3 parts (91.1%) of 2-methoxy-α-[(2-methylphenyl)amino]-1-naphthalenecarbothioamide; mp. 162.2° C.

A mixture of 17.6 parts of 2-methoxy-α-[(2-methylphenyl)amino]-1-naphthalenecarbothioamide, 78 parts of a sodium hydroxide solution 2 N and 200 parts of methanol is stirred and heated to 50° C. After cooling to 0° C., there is added dropwise, during a 30 minutes-period, a solution of 37.2 parts of hydrogen peroxide in 64 parts of methanol at 0° C. Upon completion, the mixture is allowed to reach room temperature: an exothermic reaction occurs (temp. rises to 35° C.). After reaction, stirring is continued overnight at room temperature. The reaction mixture is cooled to 0° C. and neutralized with a sulfuric acid solution 10%. The precipitated product is filtered off and dissolved in 375 parts of trichloromethane. The solution is dried, filtered and evaporated. The residue is dissolved in 50 parts of a mixture of trichloromethane and methanol (95:5 by volume). The undissolved product is filtered off and dried, yielding 13.6 parts (82%) of 2-methoxy-α-[(2-methylphenyl)amino]-1-naphthaleneacetamide; mp.194.6° C.

EXAMPLE XI

To a stirred solution of 42.8 parts of 2-methylbenzenamine in 375 parts of trichloromethane are added dropwise 41.8 parts of 2,6-dichlorobenzoyl chloride at reflux temperature. Then there are added 1.2 parts of N,N-dimethyl-4-pyridinamine and stirring is continued for 3 hours at reflux. The reaction mixture is allowed to cool to room temperature overnight and diluted with 375 parts of trichloromethane. The organic phase is washed successively with 100 parts of water, 100 parts of a hydrochloric acid solution 3 N and again 100 parts of water, dried, filtered and evaporated. The residue is crystallized from 200 parts of 2-propanol, yielding 40.6 parts (72.5%) 2,6-dichloro-N-(2-methylphenyl)benzamide; mp. 182.5° C.

A mixture of 7 parts of 2,6-dichloro-N-(2-methylphenyl)benzamide and 5.2 parts of phosphor pentachloride is stirred and heated for 10 minutes in an oil-bath at 80° C. Methylbenzene is added and the whole is evaporated in vacuo. The residue is dissolved in methylbenzene and evaporation in vacuo is continued to remove the last traces of phosphoryl chloride, yielding 7.45 parts of N-[chloro(2,6-dichlorophenyl)methylene]-2-methylbenzenamine as an oily residue.

To a stirred solution of 7.45 parts of N-[chloro(2,6-dichlorophenyl)methylene]-2-methylbenzenamine in 150 parts of trichloromethane is added a solution of 4.88 parts of potassium cyanide and 8.5 parts of N,N,N-triethylbenzenemethanaminium chloride in 8 parts of water while stirring vigorously. Stirring is continued for 30 minutes at room temperature. The organic phase is separated, washed twice with water, dried, filtered and evaporated. The residue is dissolved in petroleumether and the solution is decanted from some insoluble tar. The petroleumether is evaporated in vacuo. The residue is purified by column-chromatography over silica gel using trichloromethane as eluent. The pure fractions are collected and the eluent is evaporated. The residue is crystallized from 17.5 parts of petroleumether, yielding 2.8 parts of 2,6-dichloro-α-[(2-methylphenyl)imino]benzeneacetonitrile; mp. 55° C.

To a stirred mixture of 2.9 parts of 2,6-dichloro-α-[(2-methylphenyl)imino]benzeneacetonitrile in 50 parts of methanol are added portionwise 0.2 parts of sodium borohydride. Upon completion the mixture is stirred during 0.5 hours and 100 parts of water are added. The precipitated produce is filtered off and recrystallized from 30 parts of 2-propanol, yielding 2.4 parts (82.1%) of 2,6-dichloro-α-[(2-methylphenyl)amino]benzeneacetonitrile; mp. 107.7° C.

EXAMPLE XII

A mixture of 43 parts of methyl 5-(α-carbamoyl-o-chlorobenzylamino)-2,4-dichlorobenzoate, 400 parts of a hydrochloric acid solution and 200 parts of glacial acetic acid is stirred and refluxed for 70 hours. The reaction mixture is cooled and the precipitated product is filtered off. It is washed on the filter with fresh water and then dissolved in ether. The ethereal solution is shaken with water and with alkaline water. The aqueous phase is separated, acidified with a hydrochloric acid solution and the product is extracted with ether. The latter is washed twice with water, dried, filtered and evaporated, yielding 34.1 parts of N-(5-carboxy-2,4-dichlorophenyl)-2-(o-chlorophenyl)glycine as a solid residue; mp. 210° C.

EXAMPLE XIII

Following the procedure of Example XII and using equivalent amounts of the appropriate starting materials, there are also prepared:

3-(α-carboxy-2,6-dichlorobenzylamino)-4-chlorohydratropic acid; mp. 199.5° C.;

3-(α-carboxy-2,6-dichlorobenzylamino)hydratropic acid; mp. 180°–184° C.;

3-(α-carboxy-o-chlorobenzylamino)-4-fluorohydratropic acid; mp. 229.3° C.;

3-(α-carboxy-o-chlorobenzylamino)-4,5-dichlorobenzoic acid; mp. 255°–263.5° C.; and 4-(4-tert-butyl-α-carboxybenzylamino)hydratropic acid; mp. 160.3° C.

EXAMPLE XIV

A mixture of 9.8 parts of 2-2-toluidino)-2-(2,3,5-trichlorophenyl)acetamide and 100 parts of potassium hydroxide in ethanol 1 N is stirred and refluxed for 96 hours. The reaction mixture is filtered and the filtrate is evaporated. The residue is taken up in water and shaken with 1,1'-oxybisethane. The aqueous phase is separated and acidified with concentrated hydrochloric acid solution: an oil is separated which solidifies on standing. The product is dissolved in 1,1'-oxybisethane. The solution is washed with water, dried, filtered and evaporated. The residue is crystallized from glacial acetic acid at room temperature, filtered off, washed with glacial acetic acid and with petroleumether and dried, yielding 5.2 parts of N-2-tolyl-2-(2,3,6-trichlorophenyl)glycine; mp. 192.6° C.

EXAMPLE XV

Following the procedure of Example XIV and using equivalent amounts of the appropriate starting materials, there are also prepared:

| $R^1, R^2, R^3$ | $R^{4,5,6}$ | melting point in °C. |
|---|---|---|
| 2,6-Cl$_2$ | 2,4-(CH$_3$)$_2$ | 167 |
| 2,6-Cl$_2$ | 3,4-(CH$_3$)$_2$ | 193.5 |
| 2,6-Cl$_2$ | 3-CF$_3$ | 172 |
| 2,6-Cl$_2$ | 3-CH$_3$, 4-Cl | 161 |
| 2,6-Cl$_2$ | 2,5-(CH$_3$)$_2$ | 181 |
| 2,6-Cl$_2$ | 3-Cl, 4-CH$_3$ | 160.5 |
| 2,6-Cl$_2$ | 2-CH$_3$, 3-Cl | 189.5 |
| 2,6-Cl$_2$ | 4-Cl | 175.5 |
| 2,6-Cl$_2$ | 3-Cl | 176.5 |
| 2,6-Cl$_2$ | 2-CH$_3$, 4-Cl | 184.5 |
| 2,6-Cl$_2$ | 2-CH$_3$ | 192 |
| 2,6-Cl$_2$ | 2-OCH$_3$ | 173.5 |
| 2,6-Cl$_2$ | 2,3-(CH$_3$)$_2$ | 186.5 |
| 2,6-Cl$_2$ | 3-CH$_3$ | 162.5 |
| 2,4-Cl$_2$ | 2-CH$_3$ | 140.7 |
| 2,4-Cl$_2$ | — | 133.9 |
| 2,4-Cl$_2$ | 4-Cl | 146 |
| 2,4-Cl$_2$ | 2,6-Cl$_2$ | 131.3 |
| 2-Cl | 2,6-Cl$_2$ | 154.1 |
| 4-Cl | 2,4,6-Cl$_3$ | 148.9 |
| 2,4-Cl$_2$ | 2,4,5-Cl$_3$ | 207.4 |
| 2,6-Cl$_2$ | 3,4-Cl$_2$ | 191.1 |
| 4-Cl | 2,4,5-Cl$_3$ | 196.7 |
| 4-CH$_3$ | 2,4,5-Cl$_3$ | 195 |
| 2,6-Cl$_2$ | 2,5-Cl$_2$ | 232.9 |
| 2,4-Cl$_2$ | 3-Cl | 127.2 |
| 2,4-Cl$_2$ | 3-CH$_3$ | 128.2 |
| 2,4-Cl$_2$ | 2-Cl | 174.6 |
| 3-Cl | 2,4,5-Cl$_3$ | 167 |
| 2-Cl | 2-CH$_3$, 3-Cl | 177.2 |
| 3-Cl | 2-CH$_3$, 3-Cl | 153.3 |
| 2-Cl | 2,3-Cl$_2$ | 159.9 |
| 3-Cl | 2,6-Cl$_2$ | 129.4 |
| 3,4-Cl$_2$ | 2-CH$_3$, 3-Cl | 159.3 |
| 2-Cl | 2,5-Cl$_2$ | 203.4 |
| 3,4-Cl$_2$ | 2,5-(CH$_3$)$_2$ | 135.3 |
| 2,4-Cl$_2$ | 2,5-(CH$_3$)$_2$ | 147.1 |
| 3,4-Cl$_2$ | 2,6-Cl$_2$ | 117.7 |
| 3-Cl | 2,5-Cl$_2$ | 155.6 |
| 2-Cl | 2,4-Cl$_2$ | 184.3 |
| 3-Cl | 4-Cl | 139.4 |
| 3-Cl | 2,5-(CH$_3$)$_2$ | 123.3 |
| 2,4-Cl$_2$ | 2-CH$_3$, 3-Cl | 169.4 |
| 2-CH$_3$ | 2,4,5-Cl$_3$ | 207.9 |
| 2,6-Cl$_2$ | 2,4,5-Cl$_3$ | 245.1 |
| 3,4-Cl$_2$ | 2,3-Cl$_2$ | 175.9 |
| 2,5-Cl$_2$ | 2,4,5-Cl$_3$ | 188.6 |
| 2-Cl | 2-Cl, 5-CF$_3$ | 201.4 |
| 2-Cl | 2-CH$_3$, 4-Cl | 183.4 |
| 2-Cl | 3,5-Cl$_2$ | 172.7 |
| 2,6-Cl$_2$ | 3,5-Cl$_2$ | 184.2 |
| 2,6-Cl$_2$ | 2-CH$_3$, 5-Cl | 198.2 |
| 2,6-Cl$_2$ | 2-Cl, 5-CF$_3$ | 213.4 |
| 2-Cl | 2,4,5-Cl$_3$ | 200.5 |
| 2,6-Cl$_2$ | 4-Br | 183 |
| 2,6-Cl$_2$ | 4-I | 155.5 |
| 2-F | 2,4,5-Cl$_3$ | 183.7 |
| 2,6-Cl$_2$, 3-NH$_2$ | 4-Cl | 169.6 . HCl |
| 2,6-Cl$_2$ | 4-CH$_3$ | 141.3 |
| 2-Cl, 4-CH$_3$ | 2,4,5-Cl$_3$ | 183.8 |
| 2-Cl, 6-CH$_3$ | 2,4,5-Cl$_3$ | 231.1 |
| 2,6-Cl$_2$ | — | 140 |
| 2-Cl | 2-Cl, 4-CH$_3$ | 169.1 |
| 2-Cl | 3-CH$_3$ | 124.6 |
| 2-Cl | 3,4-(CH$_3$)$_2$ | 134.6 |
| 2-Cl | 3-Cl | 149.1 |
| 2-Cl | 2,5-(CH$_3$)$_2$ | 153.5 |
| 2-Cl | 2-Cl | 190.2 |
| 2-Cl | 2-CH$_3$ | 149.4 |
| 2-Cl | 2-CH$_3$, 4-Cl | 149.5 |
| 2-Cl | 3-Cl, 4-CH$_3$ | 150.6 |
| 2-Cl | 3,4-Cl$_2$ | 152.8 |
| 2-Cl | 2,3-(CH$_3$)$_2$ | 130.7 |
| 2-Cl | 4-CH$_3$ | 80.4 2-propanolate |
| 2-Cl | 4-Cl | 138.2 |
| 2,6-Cl$_2$ | 2-Cl | 195.7 |
| 2,6-Cl$_2$ | 2-Cl, 4-CH$_3$ | 188.1 |
| 2,6-Cl$_2$ | 2-OCH$_3$, 5-CH$_3$ | 163.5 |
| 2,3,4-Cl$_3$ | 2-CH$_3$ | 177.8 |
| 2,6-Cl$_2$ | 2,6-(CH$_3$)$_2$ | 194.2 |
| 2,3,6-Cl$_3$ | 2,5-(CH$_3$)$_2$ | 190.1° |
| 2,3,6-Cl$_3$ | 4-Cl, 3-CH$_3$ | 158.2 |
| 2,3,6-Cl$_3$ | 3-CF$_3$ | 160.7 |
| 2,3,6-Cl$_3$ | 2,5-Cl$_2$ | 205.6 |
| 2,3,6-Cl$_3$ | 3,5-Cl$_2$ | 166.4 |
| 2,3,6-Cl$_3$ | 4-Br | 171.2 |
| 2,3,6-Cl$_3$ | — | 139.2 |

EXAMPLE XVI

A mixture of 12.7 parts of 2-(2,6-dichlorophenyl)-2-(2-naphthylamino) acetamide and 250 parts of potassium hydroxide/ethanol 1 N is stirred and refluxed for 48 hours. The reaction mixture is evaporated. The oily residue is dissolved in 400 parts of water and the solution is acidified with concentrated hydrochloric acid solution. The sticky product is extracted with 1,1'-oxybisethane. The extract is washed twice with water, dried and evaporated. The oily residue is triturated three times in petroleumether. The solid product is filtered off and recrystallized from 50 parts of glacial acetic acid. The product is washed with petroleumether, dried and dissolved in 80 parts of 1,1'-oxybisethane. The solution is stirred with activated charcoal, filtered and the filtrate is evaporated. The oily residue solidifies on triturating in 2-propanol and petroleumether. The solid is filtered off and dried, yielding 1.6 parts of 2-(2,6-dichlorophenyl)-N-(2-naphthyl)glycine; mp. 171.7° C.

A mixture of 13.6 parts of 2-methoxy-α-[(2-methylphenyl)amino]-1-naphthaleneacetamide and 120 parts of a solution of potassium hydroxide in ethanol 1 N is stirred and refluxed for 64 hours. The reaction mixture is evaporated and the residue is taken up in 250 parts of water. The unreacted starting material "A" is filtered off and the filtrate is neutralized with glacial acetic acid. The precipitated product is filtered off and dissolved in 140 parts of 1,1'-oxybisethane. The solution is washed with 100 parts of water, dried, filtered and evaporated. The solid residue is crystallized from 40 parts of 2-propanol at 0° C. The product is filtered off and dried, yielding 4.8 parts (35.5%) of 2-methoxy-α-[(2-methylphenyl)amino]-1-naphthaleneacetic acid; mp. 187.5° C.

EXAMPLE XVII

To a stirred solution of 13.2 parts of N-(m-chlorophenyl)-2-(2,6-dichlorophenyl)glycine in 80 parts of hexamethylphosphoramide are added portionwise 2.1 parts of sodium hydride 50% and the whole is stirred for 30 minutes. Then there are added dropwise 6.9 parts of ethyl iodide and stirring is continued for 20 hours at room temperature. The reaction mixture is poured onto 320 parts of benzene. The organic layer is washed successively twice with 50 parts of water, twice with 50 parts of a sodium hydroxide solution 5% and again twice with 50 parts of water, dried, filtered and evaporated. The oily residue solidifies on standing at room temperature. The solid product is filtered off and crystallized from 2-propanol, yielding 8.9 parts of ethyl N-(m-chlorophenyl)-2-(2,6-dichlorophenyl)glycine; mp. 120.5° C.

EXAMPLE XVIII

Following the procedure of Example XVII and using equivalent amounts of the appropriate starting materials there are also prepared:

![structure: 2,6-dichlorophenyl-CH(COOR)-NH-phenyl(R4,5,6)]

| $R^{4,5,6}$ | R | melting point in °C. |
|---|---|---|
| 4-Cl | $CH_3$ | 120.5 |
| 4-Cl | $C_2H_5$ | 127.5 |
| 4-Cl | $(CH_2)_3CH_3$ | 102 |
| 4-Cl | $(CH_2)_2-N(CH_3)_2$ | 205.5 |
| 4-Cl | $(CH_2)_2O\ C_6H_5$ | 107.5 |

-continued

| $R^{4,5,6}$ | R | melting point in °C. |
|---|---|---|
| 3-Cl | $(CH_2)_3CH_3$ | 63.5 |
| 3-Cl | $(CH_2)_7CH_3$ | 76.5 |
| 3-Cl | $(CH_2)_5CH_3$ | 61.5 |
| 3-Cl | $CH_3$ | 120.5 |
| 3-Cl | $(CH_2)_2CH(CH_3)_2$ | 53 |
| 3-Cl | $CH_2CH(CH_3)_2$ | 83 |
| 3-Cl | $(CH_2)_9CH_3$ | 41.5 |
| 3-Cl | $(CH_2)_8CH_3$ | 60.5 |
| 3-Cl | $(CH_2)_6CH_3$ | 64 |
| 3-Cl | $(CH_2)_4CH_3$ | 44.5 |
| 3-Cl | $(CH_2)_2CH_3$ | 94 |
| 2-$CH_3$, 4-Cl | $(CH_2)_3CH_3$ | 100.5 |
| 2-$OCH_3$ | $(CH_2)_2CH(CH_3)_2$ | — |
| 2-$OCH_3$ | $(CH_2)_7CH_3$ | — |
| 2-$OCH_3$ | $CH_2CH(CH_3)_2$ | 55.5 |
| 2-$OCH_3$ | $C_2H_5$ | 81.5 |
| 2-$OCH_3$ | $(CH_2)_2CH_3$ | 73.5 |
| 2-$OCH_3$ | $(CH_2)_4CH_3$ | — |
| 2-$OCH_3$ | $(CH_2)_2OC_6H_5$ | 98 |
| 2-$OCH_3$ | $CH_3$ | 151.5 |
| 2-$OCH_3$ | $(CH_2)_3CH_3$ | 66.5 |
| 2-$OCH_3$ | $CH_2-C\equiv CH$ | 128.5 |
| 2-$OCH_3$ | $CH_2OC_2H_5$ | 89 |
| 2-$OCH_3$ | $(CH_2)_5CH_3$ | 46.5 |
| 2-$OCH_3$ | $(CH_2)_6CH_3$ | 39 |
| 2,3-$(CH_3)_2$ | $(CH_2)_3CH_3$ | 79 |
| 3-$CH_3$ | $(CH_2)_6CH_3$ | 46.5 |
| 4-Cl | $CH_2-C\equiv CH$ | 82 |
| 3-$CH_3$ | $(CH_2)_3CH_3$ | 55 |
| 3-$CH_3$ | $(CH_2)_7CH_3$ | 57 |
| 3-$CH_3$ | $(CH_2)_2CH(CH_3)_2$ | 45.5 |
| 3-$CH_3$ | $(CH_2)_5CH_3$ | 52.5 |
| 3-$CH_3$ | $C_2H_5$ | 95 |
| 3-$CH_3$ | $(CH_2)_2CH_3$ | 62 |
| 3-$CH_3$ | $CH_3$ | 130.5 |
| 3-$CH_3$ | $(CH_2)_8CH_3$ | 37.5 |
| 3-Cl | $(CH_2)_{10}CH_3$ | 55.5 |
| 3-$CH_3$ | $(CH_2)_{10}CH_3$ | 54.5 |
| 3-$CH_3$ | $CH_2CH(CH_3)_2$ | 81 |
| 3-$CH_3$ | $(CH_2)_9CH_3$ | <50 |
| 3-$CH_3$ | $(CH_2)_4CH_3$ | 62 |
| 4-Br | $CH_2-C\equiv CH$ | 90.4 |
| 4-Br | $(CH_2)_6CH_3$ | 39.4 |
| 4-Br | $CH_3$ | 138.2 |
| 2-$CH_3$ | $(CH_2)_3CH_3$ | 50 |

EXAMPLE XIX

Following the procedure of Example XVII and using equivalent amounts of the appropriate starting materials there are also prepared:
methyl 2-(2-chlorophenyl)-N-(2,4,5-trichlorophenyl)glycine; mp. 116.3° C.;
[2-(dimethylamino)ethyl]2-(2-chlorophenyl)-N-(2,4,5-trichlorophenyl)glycine hydrochloride; mp. 206.2° C.;
methyl 2,3,6-trichloro-α-(2-methylphenylamino)benzeneacetate; mp. 122.2° C.;
ethyl 2,3,6-trichloro-α-[(2-methylphenyl)amino]benzeneacetate; mp. 104.9° C.;
propyl 2,3,6-trichloro-α-[(2-methylphenyl)amino]benzeneacetate; mp. 110.7° C.;
3-methylbutyl 2,3,6-trichloro-α-[(2-methylphenyl)amino]benzeneacetate; mp. 47.1° C.;
nonyl 2,3,6-trichloro-α-[(2-methylphenyl)amino]benzeneacetate; mp. 40° C.; and ethyl α-[(4-bromophenyl)amino]-2,3,6-trichlorobenzeneacetate; mp. 113.4° C.

EXAMPLE XX

Following the procedure of Example XVII and using equivalent amounts of the appropriate starting materials there are also prepared:

(±)-methyl 2-(2,6-dichlorophenyl)-N-(2-naphthyl)glycine; mp. 143° C. and (2-dimethylaminoethyl) 2-(2,6-dichlorophenyl)-N-(2-naphthyl)glycine; mp. 98.5° C.

EXAMPLE XXI

A mixture of 7.6 parts of methyl N-(p-bromo-α-carbamoylbenzyl) anthranilate, 200 parts of potassium hydroxide/2-propanol 1 N and 20 parts of water is stirred and refluxed for 24 hours. The reaction mixture is evaporated. The residue is dissolved in 100 parts of water. The solution is acidified with concentrated hydrochloric acid solution. The precipitated product is filtered off and crystallized from 100 parts of glacial acetic acid (activated charcoal). The latter is filtered off and 100 parts of water are added to the filtrate. After standing at room temperature, the product is precipitated again. It is filtered off and dried, yielding 4.7 parts of N-(p-bromo-α-carboxybenzyl)anthranilic acid; mp. 216.1° C.

EXAMPLE XXII

Following the procedure of Example XXI and using equivalent amounts of the appropriate starting materials there are also prepared:

N-(α-carboxy-p-chlorobenzyl)anthranilic acid; mp. 203.7° C.;

N-(α-carboxy-3,4-dichlorobenzyl)anthranilic acid; mp. 212.5° C. and

N-(α-carboxy-2,4-dichlorobenzyl)anthranilic acid; mp. 195.6° C.

EXAMPLE XXIII

To a stirred and refluxed solution of 40 parts of ethanol, 25 parts of water and 2 parts of sodium hydroxide are added 5 parts of ethyl 2-(o-methoxyphenyl)-N-(2,4,5-trichlorophenyl)glycine and stirring at reflux temperature is continued for 4 hours. The reaction mixture is evaporated. The residue is dissolved in 250 parts of water. The solution is shaken with 80 parts of ether and the aqueous phase is acidified with concentrated hydrochloric acid solution. The product is extracted twice with 80 parts of ether. The combined extracts are dried and evaporated. The solid residue is crystallized from 50 parts of glacial acetic acid at room temperature, yielding 3.2 parts of 2-(o-methoxyphenyl)-N-(2,4,5-trichlorophenyl)glycine; mp. 188.3° C.

EXAMPLE XXIV

Following the procedure of Example XXIII and using equivalent amounts of the appropriate starting materials there is also prepared:

N-(3,4-dichlorophenyl)-2-(o-methoxyphenyl)glycine isopropyl alcoholate; mp. 118.1° C.

EXAMPLE XXV

5 Parts of 2-(o-methoxyphenyl)-N-(2,4,5-trichlorophenyl) glycinonitrile are dissolved in 80 parts of absolute ethanol while warming. After cooling to 5° C., the mixture is saturated with gaseous hydrogen chloride (15 minutes) and further stirred overnight at room temperature. The mixture is heated to reflux and stirred and refluxed for 2 hours. The reaction mixture is cooled and allowed to stand for 24 hours at room temperature. The whole is filtered and the filtrate is evaporated. The solid residue is triturated in 2-propanol, filtered off again and recrystallized from 2-propanol at 0° C., yielding 2.9 parts of ethyl 2-(o-methoxyphenyl)-N-(2,4,5-trichlorophenyl)glycine; mp. 92.7° C.

EXAMPLE XXVI

Following the procedure of Example XXV and using equivalent amounts of the appropriate starting materials there are also prepared:

N-[o-chloro-α-(ethylcarbonyl)benzyl]sulfanilic acid; mp. 210.7° C. and ethyl N-(3,4-dichlorophenyl)-2-(o-methoxyphenyl)glycine; mp. 81.5° C.

EXAMPLE XXVII

Gaseous hydrogen chloride is introduced for 11 hours through a stirred and refluxing solution of 17.3 parts of (±)-2-(2,6-dichlorophenyl)-N-(2-naphthyl)glycine in 96 parts of methanol. The reaction mixture is allowed to cool overnight to room temperature. The precipitated product is filtered off and crystallized from methanol, yielding 6.4 parts of (±)-methyl 2-(2,6-dichlorophenyl)-N-(2-naphthyl) glycine; mp. 143.5° C.

EXAMPLE XXVIII

To a stirred solution of 34 parts of (±)-2-(2,6-dichlorophenyl)-N-(2-naphthyl)glycine in 480 parts of ether is added a solution of 13.2 parts of (−)-α-methylbenzylamine in 80 parts of ether at room temperature. The precipitated product is filtered off and crystallized several times from acetonitrile, till a constant rotation, yielding 0.6 parts of (−)-2-(2,6-dichlorophenyl)-N-(2-naphthyl)glycine (−)α-methylbenzylamine salt; mp. 152.7° C.; $\alpha_D^{20}$ −147.6° (1% in chloroform).

To a stirred solution of 34 parts of (±)-2-(2,6-dichlorophenyl)-N-(2-naphthyl)glycine in 480 parts of ether is added a solution of 13.2 parts of (−)-α-methylbenzylamine in 80 parts of ether. The precipitated product is filtered off and crystallized several times from acetonitrile till a constant rotation is measured. The product is shaken with hydrochloric acid solution 2 N and with ether. The latter is dried and evaporated. The residue solidifies on scratching in petroleumether, yielding 6 parts of (−)2-(2,6-dichlorophenyl)-N-(2-naphthyl)glycine; mp. 94.5° C.; $\alpha_D^{25}$ −245° (1% in chloroform).

To a stirred solution of 28.8 parts of (±)-2-(2,6-dichlorophenyl)-N-(2-naphthyl)glycine in 640 parts of ether is added a solution of 10 parts of (+)-α-methylbenzylamine in 80 parts of ether at room temperature. The precipitated product is filtered off and recrystallized three times from acetonitrile, yielding 11.9 parts of (+)-2-(2,6-dichlorophenyl)-N-(2-naphthyl)glycine (+) α-methylbenzylamine salt; mp. 151°–153° C.; $\alpha_D^{20}$ +159.5° (5% in chloroform)

To a stirred solution of 28.8 parts of (±)-2-(2,6-dichlorophenyl)-N-(2-naphthyl)glycine in 640 parts of ether is added a solution of 10 parts of (+)-α-methylbenzylamine in 80 parts of ether. The crystallized salt is filtered off and crystallized three times from acetonitrile, till a constant rotation is measured. The acid is liberated from the salt on shaking in hydrochloric acid solution 2 N and ether. The ether layer is dried and evaporated. The residue solidifies on scratching in petroleumether, yielding 7.1 parts of (+)-2-(2,6-dichlorophenyl)-N-(2-naphthyl)glycine; mp. 95° C.; $\alpha_D^{25}$ +246.1° (1% in chloroform).

EXAMPLE XXIX

A mixture of 8.62 parts of 2,3,6-trichloro-α-[(2-methylphenyl)amino]benzeneacetic acid, 25 parts of a sodium hydroxide solution 1 M in water and 100 parts of distilled water is stirred for 30 minutes at room temperature. The resulting solution is evaporated to dry, methylbenzene is added and evaporation is continued. The residue is suspended in 2,2'-oxybispropane. The product is filtered off and crystallized from acetonitrile, yielding 7 parts of sodium 2,3,6-trichloro-α-[(2-methylphenyl)amino]benzeneacetate; mp. 203.1° C.

To a stirred solution of 8.62 parts of 2,3,6-trichloro-α-(2-methylphenyl)benzeneacetic acid in 175 parts of 1,1'-oxy-bisethane are added 2.62 parts of 2,2'-iminobis[ethanol] and the whole is stirred for 1 hour at room temperature. The precipitated product is filtered off and stirred in 70 parts of 1,1'-oxybisethane. It is filtered off again and dried, yielding 10 parts of 2,3,6-trichloro-α-[(2-methylphenyl)amino]benzeneacetic acid compound with 2,2'-iminobis[ethanol] (1:1); mp. 145.2° C.

EXAMPLE XXX

A mixture of 3 parts of ethyl α-[(4-bromophenyl)amino]-2,3,6-trichlorobenzeneacetate and 4.5 parts of 2-chloroacetyl chloride is stirred for 4 hours at 80° C. The mixture is taken up twice in methylbenzene and the latter is evaporated each time. The oily residue solidifies on triturating in petroleumether. The latter is decanted and the residue is crystallized from 2,2'-oxybispropane. The product is filtered off and dried, yielding a first fraction of 1.7 parts of ethyl α-[(4-bromophenyl) (2-chloroacetyl)-amino]-2,3,6-trichlorobenzeneacetate; mp. 140.8° C. The mother liquor is concentrated and a second fraction of 1.2 parts of ethyl α-[(4-bromophenyl) (2-chloroacetyl)amino]-2,3,6-trichlorobenzeneacetate is filtered off.

What is claimed is:

1. A chemical compound selected from the group consisting of an α-amino-phenylacetic acid derivative having the formula:

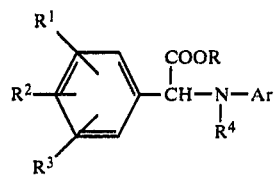

and the phytopharmaceutically acceptable salts and stereochemically isomeric forms thereof, wherein:
R is selected from the group consisting of hydrogen, and $(C_1-C_{20})$-alkyl;
Ar is selected from the group consisting of phenyl and substituted phenyl, said substituted phenyl having from 1 to 3 substituents each independently selected from the group consisting of halo, lower alkyl, lower alkyloxy, trifluoromethyl, carboxy, and carboxy(lower alkyl);
$R^1$ is selected from the group consisting of halo, lower alkyl and lower alkyloxy, and trifluoromethyl;
$R^2$ and $R^3$ are each independently selected from the group consisting of hydrogen, halo, lower alkyl, lower alkyloxy, nitro, cyano and amino; and
$R^4$ is a member selected from the group consisting of hydrogen, and lower alkyl.

2. A compound according to claim 1 wherein said $R^1$ is selected from the group consisting of 2-halo, 2-alkyloxy and 2-alkyl, said $R^2$ and $R^3$ are each independently selected from the group consisting of hydrogen, halo, lower alkyl, lower alkyloxy and amino and said $R^4$ is hydrogen.

3. A compound according to claim 2 wherein said $R^1$ is selected from the group consisting of 2-halo and 2-lower alkyloxy, $R^2$ is 6-halo, said $R^3$ is selected from the group consisting of hydrogen, halo, lower alkyl, lower alkyloxy and amino and said $R^4$ is hydrogen.

4. A compound according to claim 3 wherein said $R^1$ is selected from the group consisting of 2-halo and 2-lower alkyloxy, $R^2$ is 6-halo, said $R^3$ is 3-halo and said $R^4$ is hydrogen.

5. A compound according to claim 4 wherein said $R^1$ is 2-chloro, said $R^2$ is 6-chloro, said $R^3$ is 3-chloro and said $R^4$ and said R are hydrogen.

6. A compound selected from the group consisting of N-2-tolyl-2-(2,3,6-trichlorophenyl)glycine and the phytopharmaceutically acceptable salts and stereochemically isomeric forms thereof.

7. A compound selected from the group consisting of N-phenyl-2-(2,3,6-trichlorophenyl)glycine and the phytopharmaceutically acceptable salts and stereochemically isomeric forms thereof.

* * * * *